Figure 1:
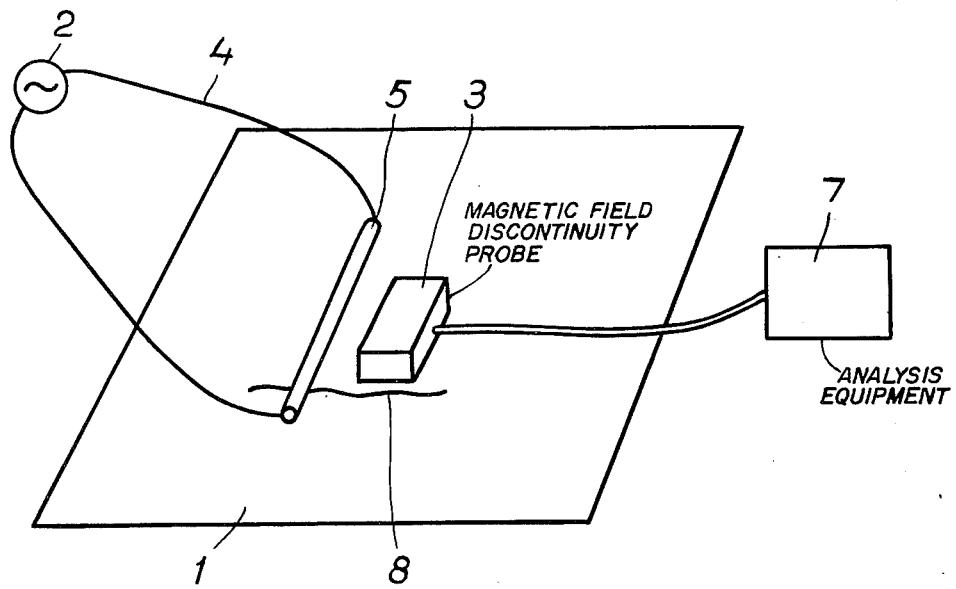

United States Patent
Bergstrand

[11] 3,967,193
[45] June 29, 1976

[54] APPARATUS FOR ELECTROINDUCTIVELY DETECTING DISCONTINUITIES BELOW THE SURFACE OF A METAL OBJECT

[75] Inventor: Carl Gunnar Bergstrand, Skultuna, Sweden

[73] Assignee: Allmanna Svenska Elektriska Aktiebolaget, Vasteras, Sweden

[22] Filed: July 14, 1972

[21] Appl. No.: 272,020

[30] Foreign Application Priority Data
July 15, 1971 Sweden.............................. 9188/71

[52] U.S. Cl. .............................................. 324/37
[51] Int. Cl.² ....................................... G01R 33/12
[58] Field of Search ............................... 324/37, 40

[56] References Cited
UNITED STATES PATENTS
2,255,053  9/1941  Gunn .................................... 324/40
3,247,453  4/1966  Quittner................................ 324/37
3,354,385  11/1967  Wood et al. .......................... 324/37
3,694,740  9/1972  Bergstrand........................... 324/37

OTHER PUBLICATIONS

Hitachi, K. K.; Method of Electromagnetic–Chemical Non–Destructive Inspection, Publication No. 24867/69; Dec. 16, 1966.

*Primary Examiner*—Robert J. Corcoran
*Attorney, Agent, or Firm*—Kenyon & Kenyon Reilly Carr & Chapin

[57] ABSTRACT

Discontinuities in metallic objects are detected by a conductor generating a magnetic field in the objects and probe means sensitive to the magnetic field and disturbances therein caused by the discontinuities.

4 Claims, 4 Drawing Figures

APPARATUS FOR ELECTROINDUCTIVELY DETECTING DISCONTINUITIES BELOW THE SURFACE OF A METAL OBJECT

BACKGROUND OF THE INVENTION

The present invention relates to an electroinductive senser and more particularly to a means for detecting discontinuities in metallic test objects of arbitrary shape.

By discontinuities is meant here all types of cracks, recesses, cavities, enclosures of foreign particles or structural variations which may affect the quality of the metallic material to be tested.

There has for a long time been a need for the manufacture of electroinductive sensers for testing metal objects of arbitrary shape, for example billets of arbitrary profile. One problem with known electroinductive sensers has, however, made the construction of such electroinductive sensers impossible and this problem is the so-called "liftoff" problem. Briefly, the liftoff problem is that distance variations between test material and senser give such large variations in output signal from the senser that only very marked discontinuities in the material can be detected. The error-indicating signals are drowned by the liftoff signals. This problem is so great that even a slight ovality in a test material having circular section completely disrupts investigation of the material.

There are a number of solutions to this problem and as an example reference is only made to the device described in German published specification No. 1,423,980.

SUMMARY OF THE INVENTION

The present invention is based on a completely different idea. That is, that the magnetic field from a current conductor placed parallel to the surface of the test material, the conductor being straight or curved according to the circumstances, will be considerably less sensitive to distance variations between a probe sensitive to the magnetic field, which is placed close to the current conductor, and the test material. In other words, the electric output signal from the probe will be much less dependent on the distance variations, thus making it possible to discover slight discontinuities and carry out a more accurate test of the metallic material.

The explanation of this is that the magnetic field is in this embodiment extended in such a shape that the liftoff effect is minimized if the probes are placed as directed.

A means according to the present invention of the type described in the introduction is therefore substantially characterized in that a current conductor is arranged substantially parallel to the surface of the test object and connected to a current source, said conductor being arranged to generate a magnetic field in the material, and by at least one probe located near the current conductor and sensitive to magnetic fields, said probe being arranged to be moved in relation to the test object and by means of which the disturbances in the magnetic field caused by discontinuities in the test object are detected, the arrangement being such that the magnetic field generated in the test object by the current in the return conductor between the end points of the current conductor and/or connection conductor between the current conductor and current source at the probe is substantially negligible in comparison with the first-mentioned magnetic field.

In the first place the current conductor is preferably given such shape that it follows the side or sides of the test object, but it may also be flexible so that it can be made to fit the surface of the test object.

In one embodiment of the invention the current conductor is so shaped that it forms a guide rail for the probe during its movement along the test object.

In another embodiment of the invention the probe is permanently attached to the current conductor, the combination being arranged to be moved along the test object. The current conductor may then be in the form of a coil, the axis of which is substantially parallel to the part of the surface of the test object located beneath it. The movement of the combination may be carried out as a to and fro movement over the test object or as a rotary movement over the surface of the test object about an axis which may be located outside the combination.

The number of probes sensitive to magnetic fields is preferably two and these probes may be connected in a difference connection. The number of probes in one embodiment of the invention may be greater than two and the means according to the invention is therefore preferably provided with a switching mechanism by means of which selected pairs of probes can be connected in a difference connection.

The equipment for analysis of the signals from the probes sensitive to magnetic fields will not be further described here but may, for example, be of the type described in Swedish Pat. No. 179,407.

The current conductor in a means according to the invention may consist of a single conductor rail or may be composed of several current conductors.

The probes sensitive to magnetic fields may be coils, Hall elements or the like.

THE DRAWINGS

The invention will be further described in connection with the accompanying drawings in which a number of embodiments are illustrated.

Figure 2:
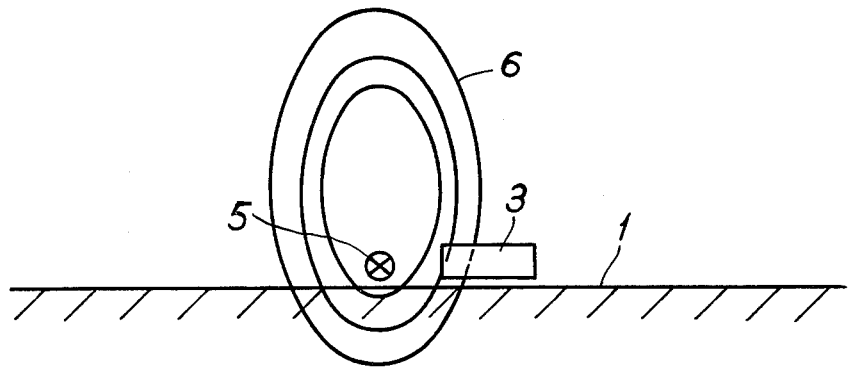
Figure 3:
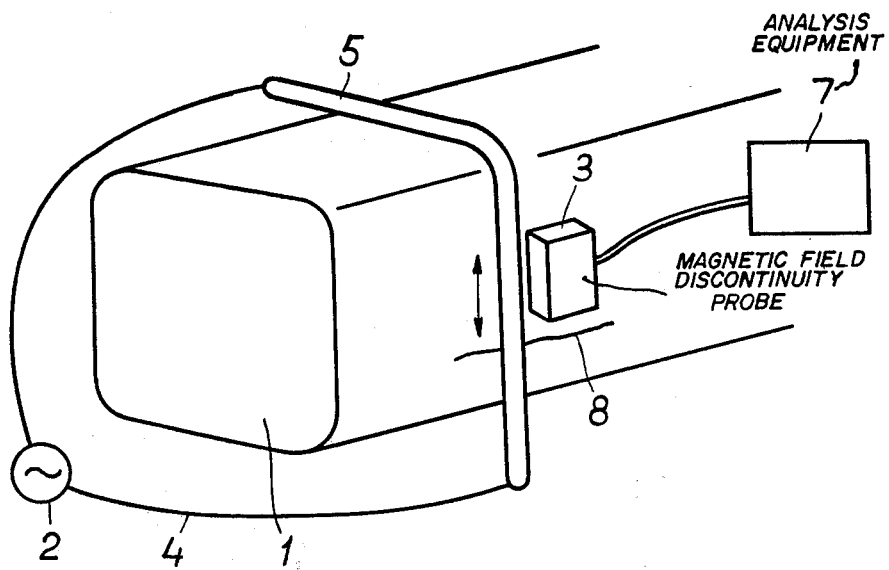
Figure 4:
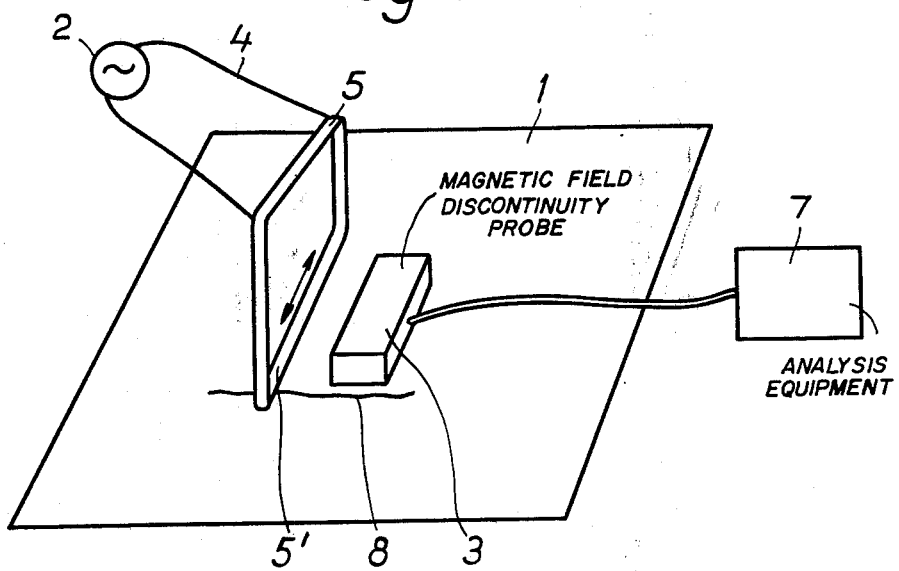

FIG. 1 shows schematically a current conductor and a probe near a test material, FIG. 2 is intended to illustrate the magnetic field near the current conductor and probe and FIGS. 3 – 4 show different embodiments of the invention.

For the sake of simplicity corresponding parts in the drawings have the same numbers.

PREFERRED EMBODIMENT

FIG. 1 shows schematically the surface of a metallic test object 1. A current generator 2 drives alternating current by way of a terminal conductor 4 through a current conductor 5 which is placed over the surface 1. Close to the current conductor 5 is a probe 3 which is sensitive to magnetic fields. This is connected to an analysis equipment 7, for example as described in the above-mentioned Swedish patent. The probe 3, possibly together with the current conductor 5, is arranged to be moved over the surface of the test material 1. When the probe 3 passes a discontinuity, such as a crack 8 in the test material, the magnetic field near the probe will be altered and this alteration is detected in the analysis equipment 7. The probe 3 preferably consists of two or more probes sensitive to magnetic fields, which are displaced from each other in the direction of movement and connected in a difference connection, the alterations in the magnetic field caused by a discontinuity being sensed in turn by the probes and detected by the analysis equipment 7.

FIG. 2 illustrates schematically the magnetic field 6 and the current conductor 5 near the probe 3.

FIG. 3 shows an embodiment of the invention for testing billets having substantially rectangular section. The current conductor 5 is curved to such a shape that it follows the two sides of the test object 1. The current source 2 feeds an alternating current through the current conductor 5 by way of the terminal conductors 4. The probe 3 which, as in FIG. 1, is connected to an analyser 7, is in this case arranged to perform a to and fro movement along the current conductor 5 close to the surface of the material 1. The current conductor 5 may then serve as guide rail for the probe 3, but the movement of this may also be guided by external members, not shown. When a discontinuity 8 is passed, the magnetic field near the probe 3 is altered and the discontinuity can thus be detected.

FIG. 4 shows an embodiment of the invention in which the current conductor 5 is designed as a "standing" coil. The axis of the coil is arranged substantially parallel to the surface of the test material located beneath it. The current conductor in this context is in fact only the part 5' of the coil which is located nearest the material 1. The magnetic field in the test object 1 from other parts of the coil is negligible in comparison with the magnetic field from the part 5' and these other parts of the coil should only be considered as terminal conductors to the current conductor. The standing coil has the advantage that the current conductor (here 5') can easily be composed of a number of single conductors.

The combination of standing coil 5 and probe 3 is arranged to be moved along the surface of the material. A crack 8 is detected in the same way as above by alterations in the magnetic field over it. The combination of coil 5 and probe 3 may therefore be arranged to be moved to and fro over the surface of the test material 1, to rotate about an axis perpendicular to the surface of the test object 1, or to rotate around the test object 1 about an axis parallel to the axis of the test object 1. The axis about which the test object rotates should preferably be located outside the combination.

What is claimed is:

1. Apparatus for electroinductively detecting discontinuities in a metal object beneath its surface and including means for generating a magnetic field in the object through its surface and a magnetic field discontinuity probe that is movable over the object's surface adjacent to said field; wherein the improvement comprises said means being formed by at least one conductor having terminal ends between which the conductor extends directly, said conductor being positioned substantially parallel to said surface and having means for connecting its terminal ends with an AC current source without substantially affecting the magnetic field generated in the object only by said conductor, said conductor forming a guide rail for the probe during its movement along the object.

2. The apparatus of claim 1 in which said conductor is movable over said surface.

3. The apparatus of claim 1 in which said object has a shape defining two adjacent angularly interrelated surfaces and said conductor is formed with a curve between its said terminal ends and substantially follows said surfaces.

4. The apparatus of claim 1 in which said conductor is formed by one side of a standing coil positioned over said surface and having an axis substantially parallel to said surface, the balance of the coil extending angularly away from said surface and forming said terminal connecting means.

* * * * *